United States Patent [19]

Wilton

[11] Patent Number: 5,512,429
[45] Date of Patent: Apr. 30, 1996

[54] ASSAY FOR ENZYME ACTIVITY

[75] Inventor: David C. Wilton, Bassett, England

[73] Assignee: British Technology Group Limited, London, United Kingdom

[21] Appl. No.: 262,355

[22] Filed: Jun. 20, 1994

Related U.S. Application Data

[63] Continuation of Ser. No. 842,339, PCT/GB90/01354, Sep. 3, 1990, abandoned.

[30] Foreign Application Priority Data

Sep. 19, 1989 [GB] United Kingdom ................. 8921156

[51] Int. Cl.$^6$ .............................. C12Q 1/00; C12Q 1/44; G01N 33/53; G01N 31/00
[52] U.S. Cl. .................. 435/4; 435/19; 435/18; 435/962; 435/975; 436/60; 436/63; 436/71; 436/501; 436/37
[58] Field of Search ................... 435/4, 19, 18, 435/962, 975; 436/501, 500, 529, 804, 825, 60, 63, 71, 501, 37; 422/55; 424/1

[56] References Cited

U.S. PATENT DOCUMENTS

| | | | |
|---|---|---|---|
| 3,983,005 | 9/1976 | Goodhue et al. | 435/19 |
| 4,195,126 | 3/1980 | Hall | 435/11 |
| 4,241,178 | 12/1980 | Eaders et al. | 435/15 |
| 4,254,082 | 3/1981 | Schick et al. | 422/55 |
| 4,311,690 | 1/1982 | Buehler et al. | 424/1 |
| 4,452,903 | 6/1984 | Lee et al. | 436/540 |
| 4,486,534 | 12/1984 | Albert et al. | 435/188 |
| 4,518,701 | 5/1985 | Khanna et al. | 436/500 |
| 4,839,298 | 6/1989 | Kay et al. | 435/175 |
| 4,945,146 | 6/1990 | Kapmeyer et al. | 436/533 |
| 5,093,045 | 3/1992 | Shoyab et al. | 260/410.8 |

FOREIGN PATENT DOCUMENTS

WO91/04338  4/1991  WIPO.

OTHER PUBLICATIONS

Vincent et al. "A protein of the Z class of liver cystosolic . . . " Journal of Biological Chemistry, 260 (27): 14521–14528, 1985.

Ransom, J. P. "Practical competititve binding . . . " St. Louis: C. V. Meslay Co., 1976, Chapters 184, pp. 2–9 & 42–53.

D. C. Wilton. "A continuous fluroesence displacement . . . " Biochemical Journal, vol. 266 No. 2, (Mar. 1990) London, pp. 435–439.

D. C. Wilton. "The fatty acid analogue 11–. . . " Biochemial Journal, vol. 270 No. 1 (15 Aug. 1990), London, pp. 163–166.

Zubay, G. Biochemistry Reading, M.A.: Addison–Wesley Publishing Co., 1983, pp. 478–479.

Wilton, D. C. "Studies on fatty acid–binding proteins . . . " Biochemical Journal 261:273–276, 1989.

Windholz, M., ed, The Merck Index, 10th Edition, Rathway, NJ: Merch and Co., 2 nc. 1983, p. 671.

Wilton "The Purification of Rat Liver fatty–acid . . . " Biochem. J. vol. 261, 1989, pp. 273–276.

Wilkinson et al. "The Binding Properties of Rat Liver Fatty . . . " Biochem J., vol. 247, 1987, pp. 485–488.

*Primary Examiner*—Douglas W. Robinson
*Assistant Examiner*—Louise N. Leary
*Attorney, Agent, or Firm*—Nixon & Vanderhye

[57] ABSTRACT

A method of assay for an enzyme catalysing the release of long chain fatty acids or, conversely, for an ester substrate for such enzymes is applicable to clinical samples and comprises removing substantially all the albumin from the clinical sample, incubating the sample after albumin removal with, for enzyme assay, an ester substrate or, for substrate assay, the enzyme, under conditions effective to release a fatty acid, causing the fatty acid to bind to a fatty acid binding protein and assaying the binding of the fatty acid to the binding protein.

24 Claims, 5 Drawing Sheets

ASSAY FOR ENZYME ACTIVITY

This is a continuation of application Ser. No. 07/842,339, filed as PCT/GB90/01354, Sep. 3, 1990, now abandoned.

BACKGROUND OF THE INVENTION

1. Field of the Invention

This invention relates to an assay applicable to clinical samples for an enzyme which catalyses directly or indirectly the release of long chain fatty acids or, conversely, for an ester substrate for such enzymes. The invention is particularly, though not exclusively, directed to the assay of lipases and phospholipases or for the ester substrates for such enzymes such as the triglyceride substrates for lipase and phospholipid substrates for the phospholipases.

2. Description of the Prior Art

Lipase, phospholipases and substrates therefor, such as the tri and diglycerides are ubiquitous and fundamental to every aspect of cell membrane function and energy transfer. The assay of these components is therefore of interest in many areas of clinical diagnosis. Thus, for example, assay of the triglyceride content of a clinical specimen can give some indication of recent dietary fat intake, and the ability of the liver to metabolise fats for energy utilisation. However presently available methods for assay of triglycerides, such as those available commercially as kits from the Sigma Chemical Co. Ltd. (Poole, Dorset, UK) rely on the measurement of glycerol released by enzyme hydrolysis. Thus, in Sigma procedure no. 405, triglycerides are extracted into isopropanol and saponified with potassium hydroxide. Liberated glycerol is then converted to formaldehyde by periodate. By reacting with acetylacetone, the formaldehyde forms yellow diacetyldihydrolutidine, which is measured colorimetrically.

In Sigma procedures nos. 336, 337, 339 and 334 glycerol is released from tryglyceride enzymatically using lipase, and glycerol is further reacted with ATP to form glycerol-1-phosphate. The four methods then differ only in the way by which the glycerol-1-phosphate is further reacted to produce a change in absorbance which can be measured spectrophotometrically. Such assays, when applied to clinical samples, suffer from the disadvantage that as glycerol itself is a product of cell metabolism, assay of the glycerol content if a blood specimen may not give an accurate picture of the circulating triglyceride levels in the subject (see Cole, Clin. Chem. 36/7, 1267–1268 (1960). There is clearly a need for the development of alternative means for assaying triglycerides that give accurate results at low concentrations or in small clinical blood specimens.

There is also a need for a rapid and accurate assay at low concentrations of lipase activity. Thus in clinical diagnosis, there is a need for the reliable detection of pancreatitis, particularly in relation to acute abdominal emergencies. Confirmation of a diagnosis of pancreatitis depends on the detection of elevated levels of pancreatic enzymes in the blood, particularly amylase and lipase, but this is normally achieved by measuring amylase levels. Amylase is not an ideal marker, because due to its small size it is partly filtered by the kidneys and levels in the pancreas may therefore be affected by kidney dysfunction. Elevated blood levels of amylase may also result from disorders of the parotid glands, which produce large amounts of salivary amylase. Lipase is potentially a better alternative, see M. Ventrucci et al., Digestive Diseases and Science 34, 39–45 (January 1989), which also contains references to assays of this kind. However, the clinical assays which have so far been developed for this enzyme are both slow and insensitive. Sigma procedure no. 800 for the measurement of lipase activity in serum is typical. Using olive oil as substrate for the enzyme, the quantity of fatty acids formed is measured by titration with dilute standardised sodium hydroxide solution. The quantity of alkali required to reach the thymolphthalein endpoint is proportional to lipase activity.

This method is clearly not suitable for use as an emergency clinical procedure. A rapid and sensitive assay for serum lipase is therefore also required.

SUMMARY OF THE INVENTION

It has now been found that such enzymes and their substrates can be assayed in clinical samples, such as serum, rapidly and sensitively by causing the enzyme to act on a substrate to release fatty acid(s), and then detecting or measuring the binding of the released fatty acids to a protein which binds fatty acids with high affinity (having a dissociation constant of $10^{-5}$M or less). Such a protein is very desirably that known as fatty acid binding protein (FABP), which is a natural product extractable, for example, from the liver of animals. Hereinafter the invention is described with reference to FABP but it will be understood that other binding proteins which bind fatty acids with such high affinity could be substituted for FABP and are therefore included within the term "a fatty acid binding protein". In addition, the invention is described with reference to serum as the clinical specimen, although it will be understood that the invention is applicable to other clinical specimens such as whole blood and plasma as well as to partially-purified fractions derived from these. The assay of the fatty acid-FABP binding interaction is most conveniently carried out by using a labelled probe, in effect a labelled fatty acid, which competes with the fatty acid released by the action of lipase for binding sites on the FABP. Conveniently the amount of free label, i.e. that which is not bound to the FABP, is then measured. However, serum albumin (SA), which is a normal constituent of clinical specimens, also possesses sites which may bind fatty acids at high affinity. When some of these binding sites are free, i.e. the total available binding capacity for fatty acids is not saturated, fatty acids released by the serum lipase are liable to bind to the SA, rather than to the FABP and hence no competition of the acid and probe for the FABP would result. Since the fatty acid must first saturate the unsaturated SA sites, the assay would be effectively de-sensitised or give a false negative result. In the invention, this problem is overcome by removing the SA from the serum sample used for the assay of enzyme or its substrate. It has been found possible to do this without releasing into the sample significant amounts of fatty acids bound to the SA.

The preferred reagent for removing the SA is 10-(1-naphthoylamino)decylagarose (NADA). It has been found that this reagent absorbs the serum albumin without having any apparent effect on the assay. NADA, being a polycyclic reagent, probably binds to SA at its bilirubin-binding sites and should not bind significantly to its high affinity fatty acid-binding sites and release fatty acids from these sites. The overall result is that NADA binds to SA without releasing significant free fatty acids into the dealbuminised serum sample. A release of fatty acids into the serum would be disadvantageous, since it would cause the assay to give a false positive or excessive reading.

Accordingly, embodying the above-stated principles, there is provided a method of assay for an enzyme catalysing directly or indirectly the release of long chain fatty acids or for an ester substrate for such enzymes in an albumin-containing clinical sample which comprises (1) removing substantially all albumin from the clinical sample;

(2) incubating the albumin-free clinical sample with an ester substrate for the enzyme to be assayed or with the enzyme which acts upon the substrate to be assayed, under conditions effective to release a fatty acid therefrom;

(3) causing the fatty acid thus released to bind to a fatty acid binding protein (FABP), and (4) assaying the binding of the fatty acid to the FABP.

In accordance with one particular preferred embodiment of the invention, there is provided a method of assay for lipase in a serum sample which comprises:

(1) removing substantially all serum albumin (SA) from the serum sample, preferably without releasing any fatty acid bound to the SA into the serum;

(2) incubating the albumin-free serum sample with a substrate for lipase which is a triglyceride fatty acid ester, under conditions effective to release a fatty acid therefrom by the action of lipase thereon;

(3) causing the fatty acid thus released to bind to a fatty acid binding protein (FABP); and (4) assaying the binding of the FABP to the fatty acid.

The invention also includes a kit for carrying out an assay of the invention, the kit comprising:

(1) a reagent for removing substantially all albumin, e.g. serum albumin (SA), from the clinical sample, and (2) fatty acid binding protein (FABP).

Preferably, the kit also includes a suitable substrate for the enzyme being assayed or an enzyme capable of hydrolysing the substrate being assayed. In the case of lipase assay, as the required fatty acid ester substrate can be merely olive oil, it need not be sold as part of the kit. Preferably a labelled probe which binds to the FABP in competition with the fatty acid is included in the kit.

The use of NADA for insolubilising SA is believed novel in its own right, whether for use in the assay or not.

DESCRIPTION OF THE PREFERRED EMBODIMENTS

The assay of the invention is applicable in principle to the serum of any mammal, but is, of course, mainly of interest in relation to humans. One purpose of the assay is to detect abnormalities of pancreatic function revealed by high concentrations of the enzyme lipase in blood and therefore in serum.

An alternative purpose is to detect the presence of a phospholipase in the serum, whether a phospholipase A2 which can directly hydrolyse phospholipids to long chain fatty acids or a phospholipase C which hydrolyses phospholipids to diacyl glycerols which themselves can be readily hydrolysed to release long chain fatty acids by the action of excess lipase. In the latter case delipidisation of the serum would be required to remove other potential lipase substrates, i.e. the triglycerides. Yet a further purpose is to detect and/or monitor the concentration of triglycerides in the blood. The assay is also applicable to the assay of cholesterol esters in serum using an appropriate cholesterol esterase.

In the assay, serum albumin (SA) is first removed from the sample. As explained above, it is preferred to do this by using a reagent which binds to the SA at a binding site other than its fatty acid binding site, immobilising the reagent-SA complex, and separating this immobilised complex from serum.

The reagent for removal of the SA will usually comprise a bulky group sterically to prevent access of the reagent to the fatty acid binding site, together with a long chain hydrophobic group and will conveniently be coupled to agarose. Obviously, compounds which are unstable are to be avoided.

The preferred reagent, 10-(1'-naphthoylamino)decylagarose (NADA) has the formula:

CONH(CH$_2$)$_{10}$NH-agarose

This compound is known per se, see D. C. Wilton, Biochem J. 261, 273–276 (1989), where its use for purifying fatty acid binding protein (FABP) is described. This gelatinous insolubilising reagent appears to have no effect on lipase concentration. It has a high binding capacity of about 5 mg/ml. of gel. The binding is substantially instantaneous, allowing the serum simply to be mixed with the gel and the bound material removed by centrifugation. Alternatively a micro-column of NADA could be used.

The corresponding dansyl compound:

SO$_2$NH(CH$_2$)$_{10}$NH-agarose can also be used, but is unstable to light over extended periods.

Other methods can be used to remove the SA. For example an immobilised antibody to SA could be used. It is also possible to use other reagents, known to bind to the bilirubin- or haem-binding sites of SA, such as 5-butyl-1-cyclohexylbarbituric acid, and couple them to a support material.

It is possible also, although less preferred, to remove the SA with a reagent which binds at the fatty acid binding site. In evaluating the result of the assay, allowance would then have to be made for possible displacement of fatty acids already bound to the SA. A column of oleoyl- or palmityl-ω aminoalkylaminoagarose is suitable, see T. Peters et al., J. Biol. Chem. 248, 2447–2451 (1973).

In the second step of the assay, the serum sample, from which substantially all the SA has been removed in the first step, is incubated with a substrate for the enzyme to be assayed or with the enzyme which acts upon the substrate to be assayed. For example in the assay of lipase, since the lipase enzyme is specific for the hydrolysis of glyceryl esters, the substrate would almost always have to be a fatty acid ester. The term "fatty acid" as used herein means predominantly any acid having a long aliphatic chain and a carboxylic acid group. The long chain aliphatic group can be saturated or unsaturated. The length of the chain is determined by the requirement to bind to the FABP and is broadly between 10 and 20, preferably 16 to 18 carbon atoms. It may be, for example, oleic, linoleic, palmitic, myristic or stearic acid. Any alcoholic residue in the ester will suffice, but the ester is conveniently a glyceride. The preferred ester is oleic acid triglyceride, available as olive oil.

The serum sample is incubated with the lipase substrate at any temperature effective for its enzymatic hydrolysis by lipase. Most conveniently room temperature (20°–25° C.) is used, but temperatures of from 15° to 400° C. are normally operable. It will be understood that the substrate selected in the second step of the assay will depend on the enzyme which it is wished to assay. Thus for assay of pancreatic phospholipase A2 it is appropriate to employ a substrate for that enzyme such as dioleoyl phosphatidyl glycerol or, for other phospholipase A2 sources, dioleoyl phosphatidyl choline, which substrates are capable of yielding a long chain fatty acid which can be analysed as described below. Alternatively, for assay of phospholipase C, while it is still appropriate to employ a substrate for that enzyme such as dioleoyl phosphatidylcholine, the enzyme only indirectly releases an assayable long chain fatty acid product and it is necessary to also employ an excess of an enzyme (such as a lipase) which is capable of hydrolysing the diacyl glyceride product to release a long chain fatty acid.

It will also be understood that if the assay is directed towards the determination of the presence of the substrate, rather than the enzyme itself, it is the appropriate enzyme which is added in the second step of the assay. Thus excess lipase can be used to assay the amount of triglyceride in the assay sample. Cholesterol esterase can be employed in the assay of cholesterol esters.

The fatty acid binding protein (FABP) is then added to the incubation mixture. There are various types of FABP operable. They are preferably cytosolic and are normally designated by the tissue from which they were isolated, e.g. small intestine, heart muscle, liver and adipose tissue. Hepatic FABP is preferred and is conveniently extracted from the liver of animals, for example from rats, pigs or bovines. A preferred extraction procedure is that described by D. C. Wilton, Biochem J. 261,273–276 (1989). The FABP need not be a natural product. It can be a synthetic analogue which binds acids or it may be the analogue of a natural product obtained by a recombinant DNA method, e.g. the rat liver FABP produced by expression of the gene in E. coli, see J. B. Lowe et al., J. Biol. Chem. 259, 12696–12704 (1984). Any incubation conditions effective to bind the acid released by the lipase can be used. Broadly, the same temperatures as in the hydrolysis step are operable.

It is then necessary to detect that acid-FABP binding has taken place. The preferred means of doing this is by a competition assay in which a labelled fatty acid species is caused to compete with the fatty acid released by the lipase for a limited number of binding sites on the FABP. The labelled species is herein called a "probe". It will normally comprise a label portion and long chain aliphatic portion, connected to an acid group and typically having from 9 to 19 carbon atoms excluding the acid group. The label portion can be a fluorophore, chromophore or luminophore, for example. Radiolabels are less preferred.

In a particularly preferred embodiment, the label is a polycyclic fluorophore, especially a naphthalene or anthracene having a polarity-sensitive fluorescent group. A polarity-sensitive fluorescent group is one which undergoes a change in its fluorescence emission (quantum yield and wavelength maximum) as it moves from a polar to non-polar environment. A large change in fluorescence signal at a fixed wavelength is observable as the probe moves to a polar micro-environment (the assay medium which will normally be aqueous) from the non-polar micro-environment of the FABP molecule. The probe is negatively charged and is therefore normally present as an acid salt. Particularly preferred such probes are those of formula Pc—Z—NH—$(CH_2)_n$—$X^-$ wherein:

Pc represents a naphthalene or anthracene residue;

Z represents —CO— or —$SO_2$—; and $X^-$ represents the anion of an acid group, preferably $COO^-$.

n is from 4 to 24, preferably 8 to 19, especially 8 to 12.

Salts of 11-(dansylamino)undecanoic acid (DAUDA) of formula are particularly preferred. This probe is known to bind to FABP in competition with fatty acids, see T. C. I. Wilkinson and D. C. Wilton, Biochem. J. 247, 485–488 (1987). Other fluorophores which can be used are 9-anthroyloxy fatty acids see J. Storch et al., J. Biol. Chem 264, 8708–8713 (1989), and cis-parinaric acid (a polyene fatty acid), see H. J. K. Keuper et al., Chem. Phys. Lipids 38, 159–178 (1985).

An alternative, but much less preferred, assay comprises adding to the assay medium a labelled acid, e.g. $^{14}C$ or $^3H$ radiolabelled, or one to which a chromophore has been attached, and measuring the amount of labelled acid remaining in solution after competition between the acid released by the lipase and the labelled acid for a limited amount of FABP. The labelled acid can be measured by insolubilising it on Lipidex 1000, see J. F. C. Glatz and J. H. Veerkamp, Anal. Biochem 132, 89–95 (1983), separating the Lipidex 1000 from the assay medium and determining the amount of labelled material thereon.

The competition assay species can usually be added to the assay mixture before, simultaneously with or after the fatty acid. The assay is regarded as "competitive", when one species displaces the other from the FABP to attain an equilibrum position for the reversible binding reaction. When the competing species binds to the FABP, the binding can be measured in various ways. In the case of a polarity-sensitive fluorophore, the change in fluorescence is easily monitored. Changes in the colour and intensity of a chromophore or of intensity of a luminophore are also susceptible to measurement. Alternatively, it is possible to precipitate the FABP-probe species, separate the precipitate, and measure the amount of label bound to the FABP or the amount of free label remaining in solution. This could be done by means of an immobilised antibody to the FABP, for example, or by coupling the FABP directly to an insoluble material such as agarose.

In an alternative procedure, the fatty acid ester is labelled in the acid moiety, e.g. by bonding it to a fluorescent reporter group and the amount of binding of the released fluorescent fatty acid to the FABP measured by a suitable spectral change occurring upon binding.

The following Examples illustrates the invention.

EXAMPLE 1

Removal of Serum Albumin From Serum 0.02 ml of a serum sample (obtained from the Pathology Laboratory, Southampton General Hospital) was added to 1 ml of a 50% by volume aqueous suspension of naphthoylagarose in a plastic microcentrifuge tube. The resulting mixture was agitated for 10 seconds and then centrifuged in an Eppendorf microfuge for 15 seconds. Typically 0.05 ml of the resulting supernatant was measured in the fluorescence assay.

Fluorescence Assay of Lipase Activity

A solution of buffer containing substrate and the fluorescent probe was prepared as follows. To 20 ml of 0.1M Tris buffer pH 8.0 containing 0.1M NaCl and 2.5mM $CaCl_2$ in a Sterilin tube was added 0.2 ml of 10 mg/ml olive oil in ethanol and 0.2 ml of 0.1 mM 11-(dansylamino)undecanoic acid (DAUDA) in methanol. The mixture was briefly shaken. 2 ml of this assay solution was added to a 4 ml plastic disposable fluorimeter cuvette which was then placed in a Perkin-Elmer LS3B fluorimeter at 25° C. The excitation wavelength was 350 nm and the fluorescence was measured at 500 nm. The machine was zeroed to give no fluorescence reading. 0.05 ml of a dealbuminised serum sample was added to the assay followed by 0.025 mg of FABP (typically 0.01 ml of a 2.5 mg/ml solution). The initial rate of fall in fluorescence was normally recorded over a period of up to 2 minutes.

Figure 1:
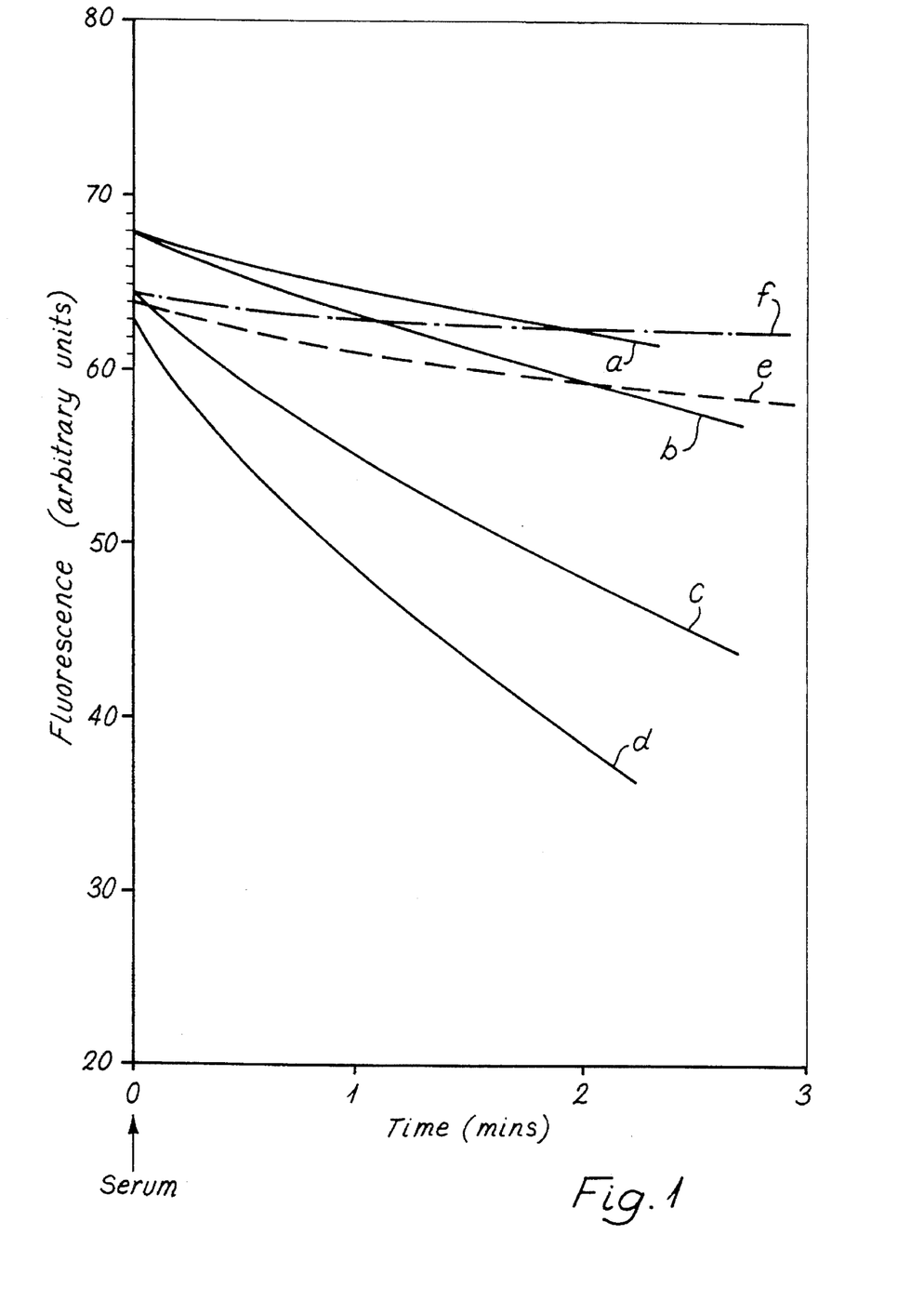

FIG. 1 shows the fluorescence displacement traces for (a) to (d) the addition of dealbuminised serum (equivalent to 0.1, 0.2, 0.4 and 0.8 µl of serum respectively) from a patient with pancreatitis, (e) a control patient (1.0 µl equivalent of normal dealbuminised serum and (f) a control, with no addition of serum sample.

The assay may be calibrated by adding known amounts of oleic acid (typically 1–10 nmoles of a solution in methanol) to the assay system in the absence of serum and recording the quantum fall in fluorescence that results.

It has been found that the assay will quantitatively measure rates of fatty acid release down to about 100 picamoles/ ml/min. and this corresponds to about 3 picakatal of enzyme activity. (The katal is a unit of measurement of the conversion rate of the enzyme and is moles/second.) Therefore for control serum samples assays may be performed on the equivalent of 0.001–0.01 ml of serum.

EXAMPLE 2

Assay of Phospholipase $A_2$

Figure 2:
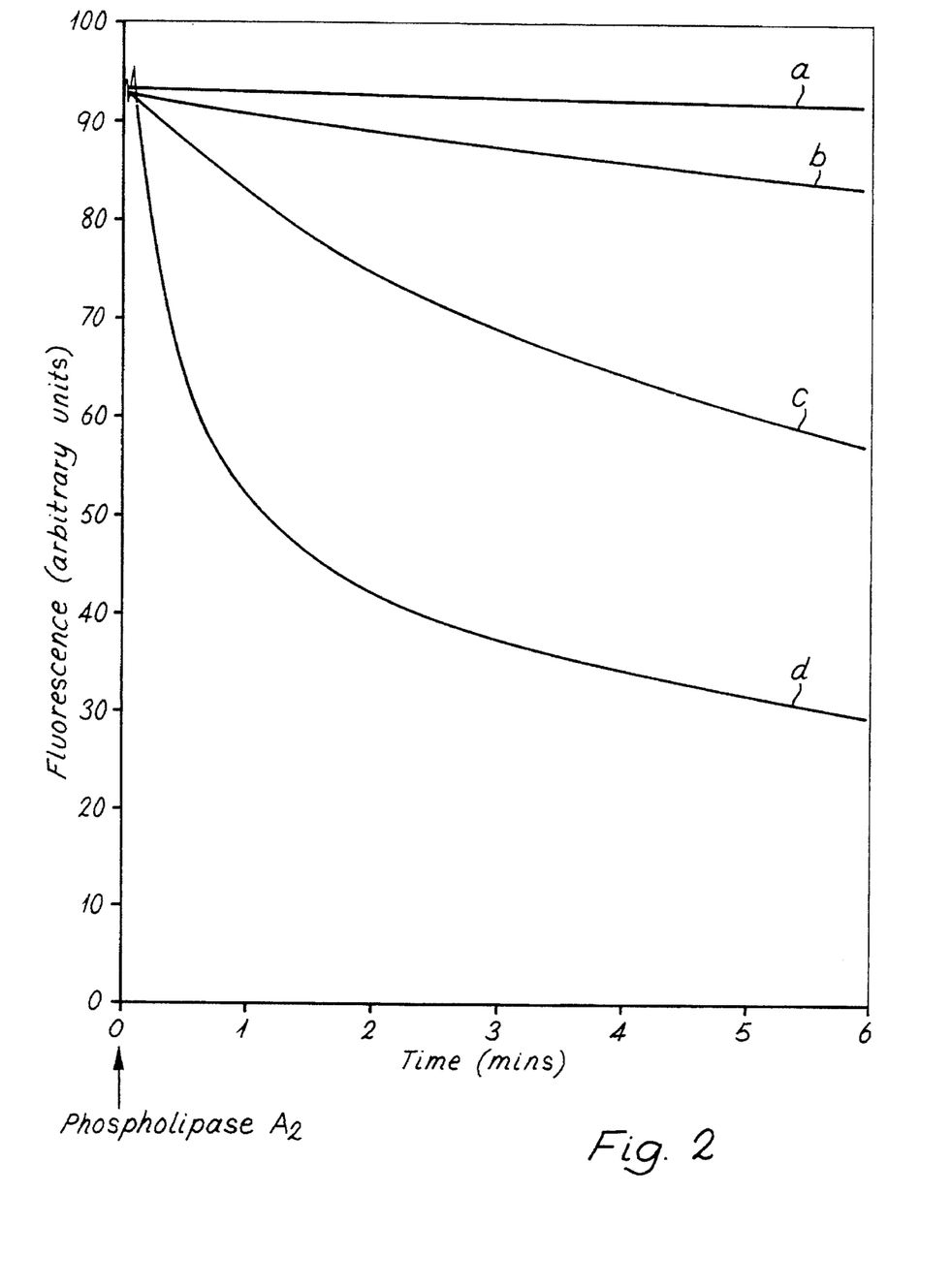

Commercially available porcine pancreas phospholipase $A_2$ (obtained from Sigma Chemical Co. Ltd.) was assayed by the fluorescence assay substantially as described in Example 1 to illustrate the applicability of the invention to assay of enzymes other than lipase which can release long chain fatty acids. The assay (2 ml) contained 0.05 mg dioleoyl phosphatidyl choline/ml, 1 µM DAUDA and 0.125 mg FABP/mi. The fluorescence displacement traces were obtained as shown in FIG. 2 illustrating (a) no addition of phospholipase $A_2$; (b) 10 ng of enzyme; (c) 100 ng of enzyme: (d) 500 ng of enzyme.

EXAMPLE 3

Assay of Triglyceride in Serum

Figure 3:
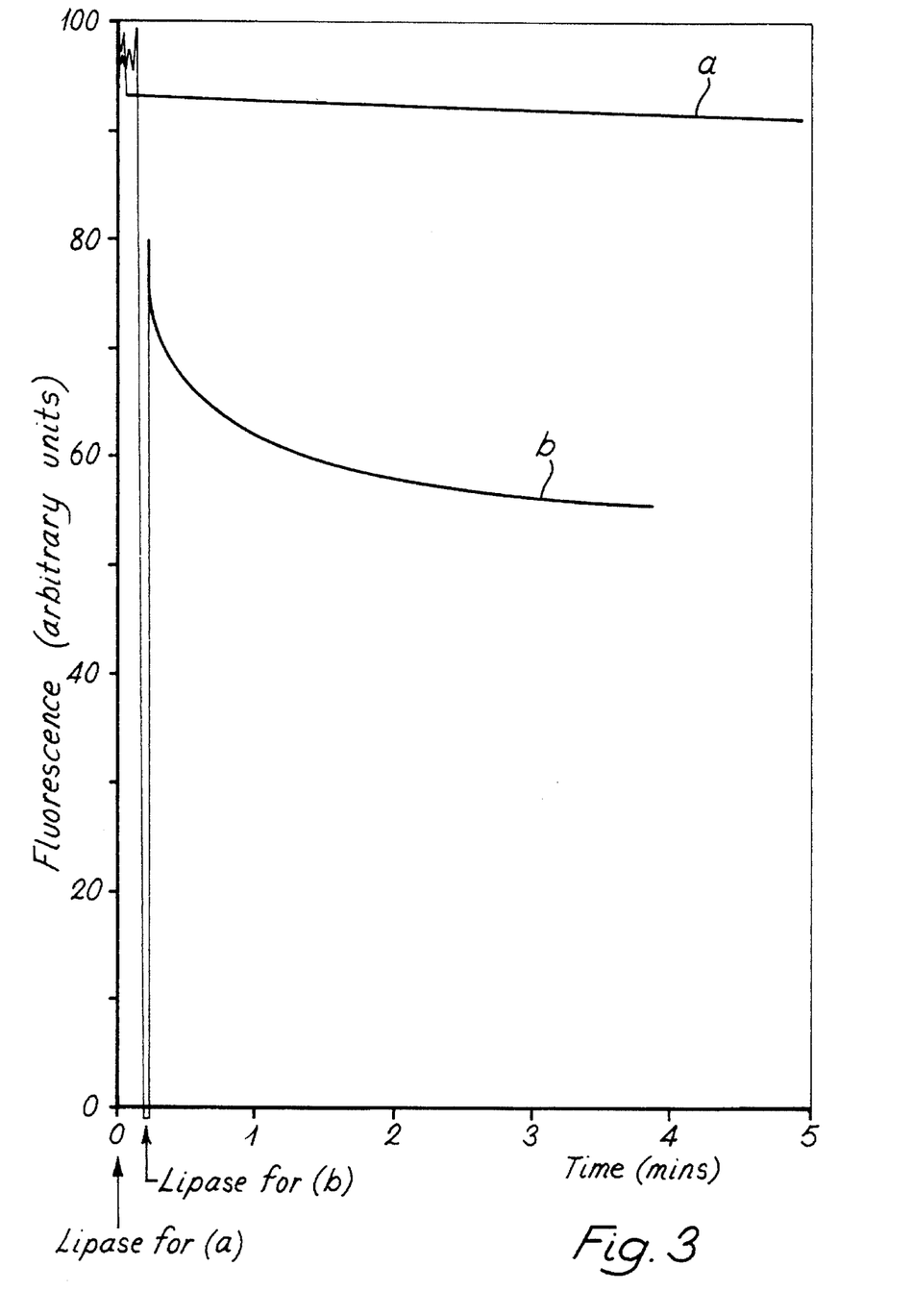

Albumin was removed from a 0.01 ml sample of serum as described in Example 1. The assay described in Example 1 was carried out (except that a $CaCl_2$-free buffer was employed) using the equivalent of 0.5 µl of dealbuminised serum which was incubated with excess lipase (derived from *Rhizopus arrhizus*) and the rapid fall in fluorescence due to DAUDA displacement observed over 3 minutes. The fluorescence displacement trace for a normal serum sample was obtained as shown in FIG. 3 illustrating the principle of specific fatty acyl substrate measurement in serum using the appropriate fatty acid measuring enzyme. Trace (a) is an $H_2O$ control, i.e. in the absence of dealbuminised serum and (b) illustrates the assay with the equivalent of 0.5 µl dealbuminised serum. The fall in fluorescence was equivalent to 1.5 nmole of fatty acid released on addition of the lipase. Assuming release of all three fatty acids from the triglyceride by the lipase, a triglyceride value in this serum of 1 mM is obtained.

EXAMPLE 4

Assay of Diglyceride Lipase Substrate

Figure 4:
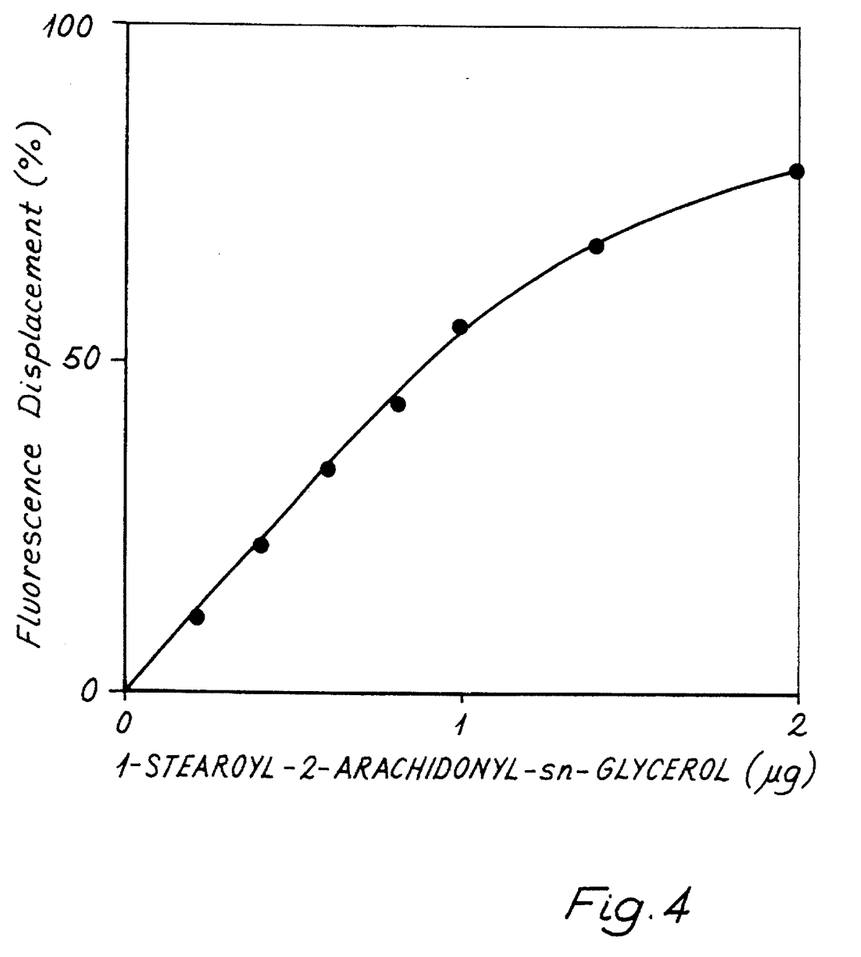

Commercially available 1-stearoyl-2-arachidonyl-sn-glycerol (obtained from Sigma Chemical Co. Ltd.) was assayed by the fluorescence assay substantially as described in Example 1 to illustrate the applicability of the invention to the assay of diacyl glycerol lipase substrates. The assay (2 ml) contained lipase, DAUDA and FABP as described in Example 3. 1 to 10 µl of 0.1 mg/ml 1-stearoyl-2-arachidonyl-sn-glycerol in ethanol was titrated into the assay and the initial fall in fluorescence was determined and is shown in FIG. 4 plotted against the amount of diglyceride added to the assay.

EXAMPLE 5

Assay of Phospholipase C

Figure 5:
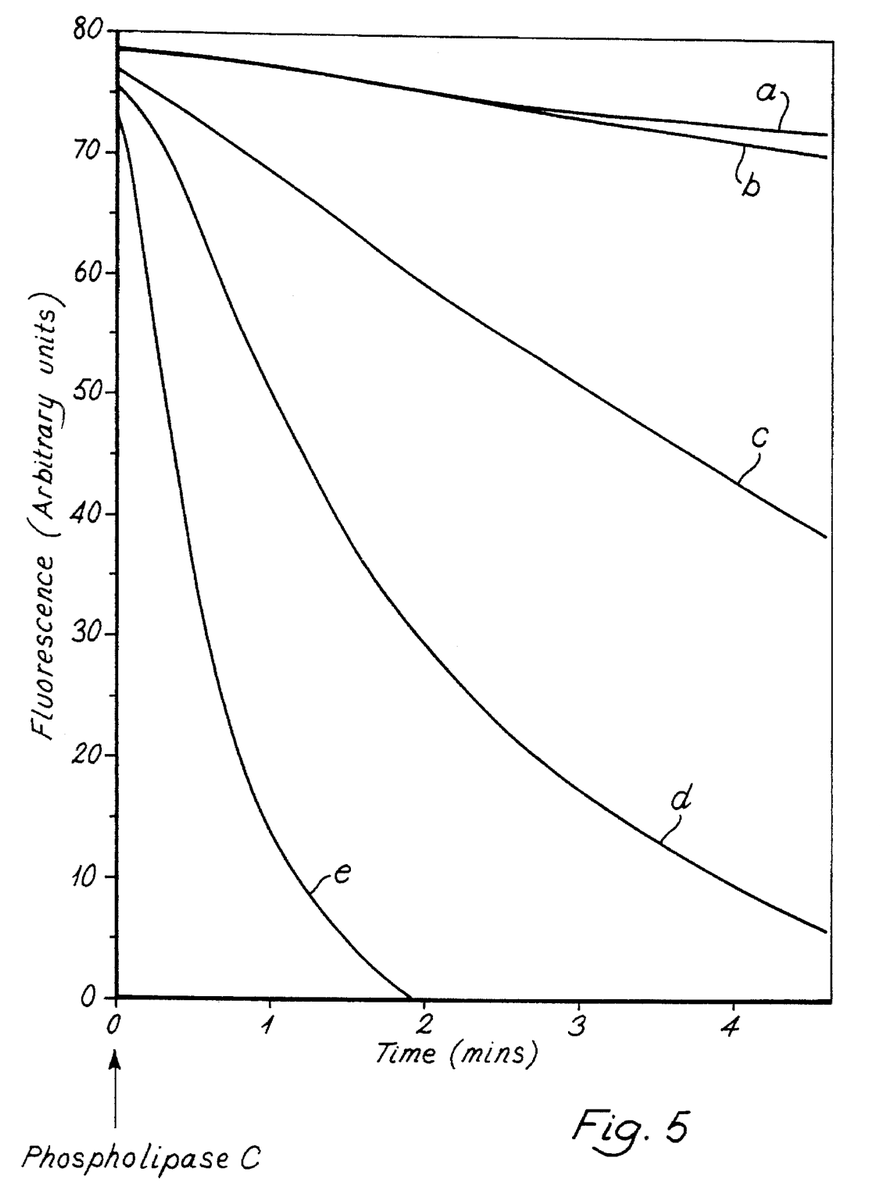

Commercially available phospholipase C from *Bacillis cereus* (quoted specific activity 2500 µ moles/min/mg; obtained from Sigma Chemical Co. Ltd) was assayed by the fluorescence assay substantially as described in Example 1 to illustrate the applicability of the invention to assay of enzymes which are capable of indirectly releasing long chain fatty acids. The assays (2 ml) contained 0.05 mg of dioleoyl phosphatidyl choline/ml (obtained from Lipid Products, UK) 1 µM-DAUDA, 0.01 mg of FABP/ml and 10 µg of purified porcine pancreatic lipase (quoted specific activity 95600 µmoles/hr/mg; obtained from Sigma Chemical Co. Ltd.). Fluorescence displacement traces were obtained as shown in FIG. 5 illustrating (a) no addition of phospholipase C; (b) addition of 2 ng of enzyme; (c) addition of 10 ng of enzyme; (d) addition of 50 ng of enzyme and (e) addition of 200 ng of enzyme.

I claim:

1. A method of assaying for an enzyme that catalyzes directly or indirectly the release of long chain fatty acids or for an ester substrate for such an enzyme in a clinical sample, which comprises the steps of:
   (1) providing a clinical sample containing an enzyme or an enzyme substrate to be assayed;
   (2) incubating said clinical sample with an ester substrate for the enzyme to be assayed or with the enzyme which acts upon the substrate to be assayed, under conditions effective to release a fatty acid therefrom;
   (3) adding a fatty acid binding protein (FABP) to cause the released fatty acid to bind to said FABP; and
   (4) assaying the binding of the FABP to the fatty acid and correlating the binding result to the amount of enzyme or substrate present in the sample.

2. A method according to claim 1, wherein said clinical sample contains albumin and substantially all albumin is removed from the clinical sample prior to incubation.

3. A method according to claim 1, wherein the binding of FABP to the fatty acid is assayed by a competitive method, in which a labelled probe which binds to the FABP in competition with the fatty acid is allowed to interact with the FABP and the free or bound labelled probe is then assayed.

4. A method according to claim 3, wherein the probe comprises a label portion attached to a long chain aliphatic portion terminating in the anion of an acid group.

5. A method according to claim 4, wherein the label is a polarity-sensitive fluorescent group which imparts to the probe a change in its fluorescent spectrum when it becomes bound to the FABP.

6. A method according to claim 4, wherein the long chain aliphatic portion has from 4 to 24 carbon atoms, excluding the acid group.

7. A method according to claim 4, wherein the aliphatic portion is an undecanoic acid residue.

8. A method according to claim 4, wherein the probe is an anion of 11-(dansylamino) undecanoic acid.

9. A method according to claim 2, wherein the albumin is removed by binding it to a reagent which does not result in significant release of fatty acids from the albumin to the clinical sample but provides for substantial removal of albumin from the sample.

10. A method according to claim 9, wherein the albumin-binding reagent is coupled to a solid phase and the insoluble material is removed.

11. A method according to claim 10, wherein the albumin-binding compound is 10-(1'-naphthoylamino) decylagarose.

12. A method according to claim 11, wherein the FABP is hepatic.

13. A method according to claim 1, wherein the clinical sample is a serum sample.

14. A method according to claim 1, wherein the assay is for lipase and step (1) comprises incubating the sample with a substrate for lipase which is a fatty acid ester under conditions effective to release a fatty acid therefrom by the action of lipase thereon.

15. A kit for carrying out an assay for an enzyme catalyzing directly or indirectly the release of long chain fatty adds or for an ester substrate for such enzymes in an albumin-containing clinical sample which comprises:

(1) a reagent for removing substantially all albumin from the clinical sample, and (2) fatty acid binding protein (FABP).

16. A kit according to claim 15, which further comprises a suitable substrate for the enzyme being assayed or an enzyme capable of hydrolyzing the substrate being assayed.

17. A kit according to claim 15 for carrying out an assay for lipase in a serum sample, which comprises (1) a reagent for removing substantially all serum albumin from the serum sample, and (2) fatty acid binding protein (FABP).

18. A kit according to claim 17, which further comprises a fatty acid ester substrate for lipase.

19. A kit according to claim 15, which further comprises a labelled probe which binds to the FABP in competition with the fatty acid.

20. A kit according to claim 19, wherein the probe comprises a label portion attached to a long chain aliphatic portion terminating in the anion of an acid group.

21. A kit according to claim 15, wherein the albumin-removing reagent is one which does not result in significant release of fatty acids from albumin but provides for substantial removal of albumin from the clinical sample.

22. A kit according to claim 21, wherein the albumin-removing reagent is a solid.

23. A kit according to claim 22, wherein the albumin-binding compound is 10-(1'-naphthoylamino) decylagarose.

24. A kit according to claim 15, wherein the FABP is hepatic.

* * * * *